(12) United States Patent
Tamai et al.

(10) Patent No.: US 8,846,807 B2
(45) Date of Patent: Sep. 30, 2014

(54) SOLVENT COMPOSITION FOR SILICONE COMPOUND

(75) Inventors: Ryoichi Tamai, Kawagoe (JP); Yasuo Hibino, Shiki (JP); Kanako Osafune, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 67 days.

(21) Appl. No.: 13/378,553

(22) PCT Filed: Jul. 9, 2010

(86) PCT No.: PCT/JP2010/061670
§ 371 (c)(1),
(2), (4) Date: Dec. 15, 2011

(87) PCT Pub. No.: WO2011/007723
PCT Pub. Date: Jan. 20, 2011

(65) Prior Publication Data
US 2012/0107513 A1    May 3, 2012

(30) Foreign Application Priority Data

Jul. 16, 2009  (JP) .................................. 2009-167556
Jul. 27, 2009  (JP) .................................. 2009-173950
Jul. 5, 2010   (JP) .................................. 2010-152586

(51) Int. Cl.
C08L 83/04   (2006.01)
C09D 183/04  (2006.01)
C07C 21/18   (2006.01)

(52) U.S. Cl.
CPC .............. *C07C 21/18* (2013.01); *C09D 183/04* (2013.01)
USPC ...................................................... 524/588

(58) Field of Classification Search
USPC ...................................................... 524/588
See application file for complete search history.

(56) References Cited

U.S. PATENT DOCUMENTS

| 6,198,010 B1 | 3/2001 | Yoshikawa et al. |
| 2005/0096246 A1 | 5/2005 | Johnson et al. |
| 2010/0004155 A1 | 1/2010 | Ishihara et al. |

FOREIGN PATENT DOCUMENTS

| JP | 2006-274173 A | 10/2006 |
| JP | 2007-332301 A | 12/2007 |
| WO | WO 2008/053656 A1 | 5/2008 |
| WO | WO 2009/089511 A2 | 7/2009 |
| WO | WO 2009/140231 A2 | 11/2009 |
| WO | WO 2010/059809 A1 | 5/2010 |
| WO | WO 2010/080544 A1 | 7/2010 |
| WO | WO 2010/085397 A1 | 7/2010 |

OTHER PUBLICATIONS

PCT/ISA/237 Form (Four (4) pages).
International Search Report including English language translation dated Oct. 5, 2010 (Five (5) pages).
European Search Report dated Nov. 28, 2012 (seven (7) pages).
Dow Corning Toray Co., Ltd. Material Safety Data Sheet, Dow Corning Toray SH 193 Fluid, Revision Date: Jan. 7, 2013 (six (6) sheets).
Chinese Office Action dated Sep. 6, 2013 (14 pages).

*Primary Examiner* — Kuo-Liang Peng
(74) *Attorney, Agent, or Firm* — Crowell & Moring LLP

(57) ABSTRACT

Disclosed is a solvent composition for silicone compounds, containing 1-chloro-3,3,3-trifluoropropene, or a solvent composition for silicone compounds, containing (A) 1-chloro-3,3,3-trifluoropropene and (B) a compound made up of at least one selected from the group consisting of 1,1,2,2-tetrafluoro-1-methoxyethane, 1,1,1,3,3-pentafluorobutane, and 1,1,2,2-tetrafluoro-1-(2,2,2-trifluoroethoxy)ethane. This solvent composition has characteristics of nonflammability and low toxicity, and handling is extremely easy. Coating properties of the silicone compound become good by mixing this solvent composition and the silicone compound.

23 Claims, No Drawings

SOLVENT COMPOSITION FOR SILICONE COMPOUND

TECHNICAL FIELD

The present invention relates to a solvent composition used for dissolving and diluting silicone compounds.

BACKGROUND OF THE INVENTION

Hitherto, as a solvent for diluting silicone compounds, hydrochlorofluorocarbons (HCFCs) such as dichloropentafluoropropane (R225), 1,1-dichloro-1-fluoroethane (R141b), etc. have widely been used, since they are nonflammable and superior in chemical and thermal stabilities. Since there is also a reason that HCFCs contain chlorine, they are high in ozone depletion potential (ODP), causing concern about the effect on the global environment. Therefore, they are scheduled to be totally abolished in the future.

In recent years, as one of solvents alternative to HCFCs, the use and the development of hydrofluorocarbons (HFCs) and hydrofluoroethers (HFEs) have been in progress. HFCs and HFEs have advantages that they are nonflammable, that they are superior in chemical and thermal stabilities and drying characteristics, that they have no ozone depletion potential, etc.

HFCs and HFEs are, however, not sufficient in silicone compound solubility. Therefore, hitherto, a method of adding various organic solvents has been studied in order to improve silicone compound solubility.

For example, in order to improve compatibility between HFEs and silicone compounds, there are disclosed a method of adding 4-30 mass % of hexamethyldisiloxane (Patent Publication 1) and a method of adding 15-60 mass % of hydrocarbons, such as normal hexane, etc., and alcohols (Patent Publication 2).

PRIOR ART PUBLICATIONS

Patent Publications

Patent Publication 1: Japanese Patent Application Publication 2006-274173
Patent Publication 2: Japanese Patent Application Publication 2007-332301

SUMMARY OF THE INVENTION

In the case of coating various articles, such as metal, resin, etc., with a silicone compound, one prepared by adjusting concentration of the silicone compound in the solvent to a predetermined concentration is used, and it is necessary to adjust concentration of the silicone compound for each of the various articles.

In the method described in Patent Publication 1, solubility of the silicone compound becomes small as the content of hexamethyldisiloxane to be added becomes low. As the content of hexamethyldisiloxane becomes high, viscosity of the solvent composition becomes high, thereby making applicability of the silicone compound inferior, lowering flash point, etc. Therefore, handling is not easy.

Similarly, also in the method described in Patent Publication 2, if the content of hydrocarbons or alcohols to be added becomes high, handling is difficult in terms of problem of flash point, and it becomes necessary to take a measure for a safe handling. For example, in the method described in Patent Publication 2, it is necessary to add 15-60 mass % of hexane, thereby causing concern of problem of flammability.

Thus, HFEs are studied as a solvent for silicone compounds, which is less in adverse effect on the environment, but compatibility between HFEs and silicone compounds is not sufficient. Therefore, it is necessary to add various organic solvents depending on the purpose of use (for example, adjusting the silicone compound concentration to be used, etc.). By that, there has been a problem of being not easy in handling in terms of safety viewpoint, such as the worsening of applicability of silicone compounds, flammability, etc.

Furthermore, if a solvent for dissolving silicone compounds is too low in boiling point, the solvent evaporates easily, from applicability, drying characteristics, etc. upon applying silicone compounds. Therefore, the application is difficult. On the other hand, if it is too high in boiling point, it is necessary to have a heating at high temperature in order to evaporate the solvent. This may cause articles, on which silicone compounds are applied, to have deformations and damages. Therefore, there is a demand for a solvent of silicone compounds, which has a boiling point close to ordinary temperature as close as possible and is easy in handling.

The present invention was made in view of the above-mentioned problems. Its task is to provide a solvent composition for silicone compounds, which is good in coating properties of silicone compounds, which has characteristics of nonflammability and low toxicity, and which is extremely easy in handling.

As a result of a repeated eager study to solve the task, the present inventors have solved the task by using 1-chloro-3,3,3-trifluoropropene, which is a fluorine-containing unsaturated hydrocarbon, as a solvent for silicone compounds.

Hitherto, there has been no report of using 1-chloro-3,3,3-trifluoropropene as a solvent for silicone compounds.

That is, the present invention provides the inventions described in [Invention 1] to [Invention 9].

[Invention 1] A solvent composition for silicone compounds, comprising 1-chloro-3,3,3-trifluoropropene.

[Invention 2] A solvent composition for silicone compounds, comprising (A) 1-chloro-3,3,3-trifluoropropene and (B) a compound made up of at least one selected from the group consisting of 1,1,2,2-tetrafluoro-1-methoxyethane, 1,1,1,3,3-pentafluorobutane, and 1,1,2,2-tetrafluoro-1-(2,2,2-trifluoroethoxy)ethane.

[Invention 3] A solvent composition for silicone compounds according to Invention 2, comprising 40-80 mass % of the 1-chloro-3,3,3-trifluoropropene and 60-20 mass % of the 1,1,2,2-tetrafluoro-1-methoxyethane.

[Invention 4] A solvent composition for silicone compounds according to Invention 2, comprising 60-80 mass % of the 1-chloro-3,3,3-trifluoropropene and 40-20 mass % of the 1,1,1,3,3-pentafluorobutane.

[Invention 5] A solvent composition for silicone compounds according to Invention 2, comprising 70-80 mass % of the 1-chloro-3,3,3-trifluoropropene and 30-20 mass % of the 1,1,2,2-tetrafluoro-1-(2,2,2-trifluoroethoxy)ethane.

[Invention 6] A silicone compound coating solution, comprising a silicone compound and a solvent composition for silicone compounds according to any one of Invention 1 to Invention 5.

[Invention 7] A silicone compound coating solution according to Invention 6, which is characterized by that the silicone compound is a straight silicone.

[Invention 8] A method for applying a silicone compound, which is characterized by that the silicone compound coating solution according to Invention 6 or Invention 7 is applied on a surface of an article, and then the solvent composition for silicone compounds in the coating solution is removed by evaporation, thereby forming a film of the silicone compound on the surface of the article.

[Invention 9] A method for applying a silicone compound according to Invention 8, which is characterized by that the article is metal or resin.

DETAILED DESCRIPTION

A solvent composition of the present invention is high in silicone compound solubility and superior in drying characteristics and uses 1-chloro-3,3,3-trifluoropropene, which has characteristics of nonflammability and low toxicity, as a solvent for silicone compounds. Therefore, it becomes possible to provide a solvent composition for silicone compounds, which has good coating properties of silicone compounds, and characteristics of nonflammability and low toxicity, and of which handling is extremely easy, without adding an organic solvent causing concern of problem of flammability, etc.

Furthermore, both cis form (Z configuration) and trans form (E configuration) of 1-chloro-3,3,3-trifluoropropene have boiling points close to ordinary temperature. Therefore, a solvent composition of the present invention has characteristics that it dissolves silicone compounds and that handling when applying a silicone compound and drying it is very easy.

Furthermore, 1-chloro-3,3,3-trifluoropropene has characteristics that ozone depletion potential (ODP) and global warming potential (GWP) are extremely small. Therefore, a solvent composition of the present invention has characteristics that global warming potential is small and greenhouse effect is small.

<Solvent Composition for Silicone Compounds>

A solvent composition for silicone compounds of the present invention is one containing 1-chloro-3,3,3-trifluoropropene.

In the following, the present invention is explained in detail.

(1-chloro-3,3,3-trifluoropropene)

Since 1-chloro-3,3,3-trifluoropropene, which is one of fluorine-containing unsaturated hydrocarbons, has a double bond, it has a high reactivity with OH radical in the atmosphere. Therefore, ozone depletion potential (ODP) and global warming potential (GWP) become extremely small. Furthermore, 1-chloro-3,3,3-trifluoropropene is nonflammable, and it is a composition having characteristics of nonflammability and low GWP.

1-chloro-3,3,3-trifluoropropene, which is used in the present invention, is a publicly-known compound mentioned in publications. For example, it can be produced by a reaction of adding hydrogen chloride to 3,3,3-trifluoropropyne, or by a dehydroiodination reaction of 3-chloro-1,1,1-trifluoro-3-iodopropane by potassium hydroxide.

Furthermore, 1-chloro-3,3,3-trifluoropropene, which is used in the present invention, can also be obtained by subjecting 1,1,1,3,3-pentachloropropane to a gas phase fluorination reaction by chromium catalyst or to a liquid phase fluorination reaction with no catalyst.

In 1-chloro-3,3,3-trifluoropropene, there exist cis form (Z configuration) and trans form (E configuration) as stereoisomers depending on the substituent type. Both isomers can be separated and purified by distillation. Boiling point of cis form (Z configuration) is 39.0° C., and boiling point of trans form (E configuration) is 21.0° C.

Furthermore, these stereoisomers are not particularly limited. It is possible to use either trans form (E configuration) or cis form (Z configuration) or a mixture.

(Other Solvent Compositions)

In the present invention, it is possible to use 1-chloro-3,3,3-trifluoropropene alone as a solvent for dissolving silicone compounds, but it is also possible to add other solvents to 1-chloro-3,3,3-trifluoropropene, depending on the use.

1-chloro-3,3,3-trifluoropropene by itself, which is used in the present invention, is very high in dissolution capacity and therefore is a preferable solvent. In the case of using 1-chloro-3,3,3-trifluoropropene alone, it may cause damages on resin members. Therefore, for the purpose of adjusting dissolution capacity, depending on the types of articles on which silicone compounds are applied, it is preferable to mix 1-chloro-3,3,3-trifluoropropene with 1,1,2,2-tetrafluoro-1-methoxyethane (HFE-254 pc), 1,1,1,3,3-pentafluorobutane (HFC-365mfc), 1,1,2,2-tetrafluoro-1-(2,2,2-trifluoroethoxy)ethane (HFE-347 pc-f), methyl nonafluoroisobutyl ether (HFE-7100), etc.

As resin members applicable in the case of mixing the above-exemplified solvents with 1-chloro-3,3,3-trifluoropropene, it is possible to mention, for example, thermosetting resins such as phenol resin, epoxy resin, polyurethane, etc., thermoplastic resins such as polyethylene (PE), polypropylene (PP), polyvinyl chloride (PVC), polytetrafluoroethylene (PTFE), acrylic resin (PMMA), polycarbonate (PC), polyamide (PA), polybutylene terephthalate (PBT), polyethylene terephthalate (PET), etc., fluororesins such as tetrafluoroethylene-ethylene copolymer (ETFE), tetrafluoroethylene-hexafluoropropylene copolymer (FEP), etc. Furthermore, as rubber members, it is possible to mention, for example, synthetic rubbers such as nitrile rubber (NBR), styrene-butadiene rubber (SBR), ethylene-propylene-diene rubber (EPDM), chloroprene rubber (CR), silicone rubber, urethane rubber, etc., or natural rubber, etc.

In the case of coating an article made of a resin member or rubber member with silicone compounds, it is possible to apply silicone compounds on the surface without adding damages to the article made of a resin member or rubber member, by adding the above-exemplified solvents to 1-chloro-3,3,3-trifluoropropene. Furthermore, it is possible to mix one kind of or at least two kinds of the above-exemplified solvents.

Next, a preferable composition proportion of each component in specific solvent compositions is explained.

It is preferable to adjust a preferable composition proportion of each component in view of solubility of silicone compounds and handling easiness (flammability, etc.) of the solvent composition for silicone compounds.

In the case of mixing 1,1,2,2-tetrafluoro-1-methoxyethane (HFE-254 pc), it is preferable as the mixing percentage to have 40-80 mass % of 1-chloro-3,3,3-trifluoropropene and 60-20 mass % of 1,1,2,2-tetrafluoro-1-methoxyethane (HFE-254 pc), respectively (see the after-mentioned Examples 2 and 3).

Furthermore, as to the mixing percentage, if the mixing percentage of 1-chloro-3,3,3-trifluoropropene is made to be greater than 80 mass %, it may cause damages on resin members such as acrylic, polycarbonate, etc. Furthermore, if the mixing percentage of 1-chloro-3,3,3-trifluoropropene is made to be less than 40 mass %, solubility of the silicone compound may become small.

In the case of mixing 1,1,1,3,3-pentafluorobutane (HFC-365mfc), it is preferable as the mixing percentage to have 60-80 mass % of 1-chloro-3,3,3-trifluoropropene and 40-20 mass % of 1,1,1,3,3-pentafluorobutane (HFC-365mfc), respectively (see the after-mentioned Example 4).

In the case of mixing 1,1,2,2-tetrafluoro-1-(2,2,2-trifluoroethoxy)ethane (HFE-347 pc-f), it is preferable as the mixing percentage to have 70-80 mass % of 1-chloro-3,3,3-trifluoropropene and 30-20 mass % of 1,1,2,2-tetrafluoro-1-(2,2,2-trifluoroethoxy)ethane (HFE-347 pc-f), respectively (see the after-mentioned Example 5).

<Silicone Compound Coating Solution>

In the present invention, it is used as a silicone compound coating solution by mixing the above-mentioned solvent composition for silicone compounds with a silicone compound. As a silicone compound used in the present invention, it is possible to use various silicones used, for example, for surface coating.

Above all, it is possible to mention straight silicone oils, such as dimethyl silicone oil, methyl phenyl silicone oil and methyl hydrogen silicone oil, in which methyl group, phenyl group and hydrogen atom are bonded as substituents, and modified silicone oils, such as reactive silicone oil and non-reactive silicone oil, which have a constituent moiety secondarily derived from straight silicone oils. A solvent composition for silicone compounds of the present invention is preferable, since it easily dissolves straight silicones in particular (see Examples).

Furthermore, it is possible to mention one containing as a main component a copolymer of aminoalkylsiloxane and dimethylsiloxane; one containing as a main component a product derived by reacting a product of the reaction of an amino group-containing silane and an epoxy group-containing silane, with a silanol group-containing polydiorganosiloxane; a silicone mixture of a silicone containing an amino group at its side chain or terminal and a polydiorganosiloxane; and a mixture of a silicone obtained by reacting an amino group-containing alkoxysilane, an epoxy group-containing alkoxysilane, and a silicone containing silanol groups at its both ends, and a non-reactive silicone; etc.

It is preferable that the percentage of a silicone compound of the present invention in the silicone solution for coating is 0.1-80 mass %, particularly 1-20 mass %. If it is less than 0.1 mass %, it is difficult to form a coating film having a sufficient film thickness. If it exceeds 80 mass %, it is difficult to obtain a coating film having a uniform film thickness.

<Application Method>

In the present invention, the above-mentioned silicone compound coating solution is applied on the surface of an article, and then the solvent composition for silicone compounds, such as 1-chloro-3,3,3-trifluoropropene, is removed by evaporation, thereby forming a film of the silicone compound on the surface of the article. As an article to which the method of the present invention can be applied, it can be applied to various materials such as metal member, resin member, ceramic member, glass member, etc. In particular, it is preferable to apply that to the needle tube portion of a needle, the spring portion of a dispenser (liquid quantitative ejection device), etc.

For example, in the case of application to the needle tube portion of a needle, etc., as a method for coating the needle tube portion of a needle with a silicone compound, it is possible to mention a dip coating method in which the needle tube portion of a needle is immersed in the silicone compound coating solution to apply it to the outer surface of the needle tube portion, and then it is permitted to stand at room temperature or under heating to evaporate the solvent composition, thereby forming a film of the silicone compound.

EXAMPLES

Next, the present invention is specifically explained by citing examples, but the present invention is not limited by these.

(Solubility Test of Silicone Compound)

According to the following method, a solubility test of the silicone compound was conducted by using the solvent composition in the present invention.

20 g of the solvent compositions shown in Table 1 to Table 5 were put into glass sample bottles, then a silicone oil (a straight silicone oil made by Shin-Etsu Chemical Co., Ltd., product name: KF-96-500CS, 100 mass %) in the amounts shown in Table 1 to Table 5 was added dropwise by 0.1 g at a time, and solubility was checked visually. The temperature of the solvent composition was set at ordinary temperature (25° C.) to conduct the solubility test. The amounts (0.1 to 80 g) of the silicone oil added, which are mentioned in Tables 2-5, represent 0.1 g, 1 g, 5 g, 30 g and 80 g of Table 1.

(Coating and Drying Characteristics Tests)

According to the following method, coating test and drying characteristics test of silicone compound were conducted by using a solvent composition for silicone compounds in the present invention. Silicone compound coating solutions, which were mixtures of solvent compositions for silicone compounds and silicone oil shown in Table 1 to Table 5, were applied on various stainless metal plates (SUS), and drying characteristics were evaluated. Furthermore, the coating films after drying (natural drying) were checked visually to evaluate coating properties. Drying characteristics and coating properties are shown in Table 1 to Table 5.

Example 1 (Examples 1-1 to 1-5) and Comparative Example 1-1

TABLE 1

| | Solvent comp. (mass %) | | Silicone oil added | Conc. of silicone compound | | Drying | Coating |
|---|---|---|---|---|---|---|---|
| | 1233Z | 1234ze(Z) | (g) | (mass %) | Solubility | characteristics | properties |
| Ex. 1-1 | 100 | 0 | 0.1 | 0.5 | dissolved | good | good |
| Ex. 1-2 | 100 | 0 | 1 | 5 | dissolved | good | good |
| Ex. 1-3 | 100 | 0 | 5 | 20 | dissolved | good | good |
| Ex. 1-4 | 100 | 0 | 30 | 60 | dissolved | good | good |
| Ex. 1-5 | 100 | 0 | 80 | 80 | dissolved | good | good |
| Com. Ex. 1-1 | 0 | 100 | 0.1 | 0.5 | undissolved | — | — |

1233Z: (Z)-1-chloro-3,3,3-trifluoropropene
1234ze (Z): (Z)-1,3,3,3-tetrafluoropropene From the results of Table 1, solubility of the silicone compound in the solvent composition of cis-form (Z)-1-chloro-3,3,3-trifluoropropene alone was good, and it was possible to prepare the silicone compound in wide concentrations. Furthermore, the coating solutions prepared by mixing the silicone compound were superior in drying characteristics and also good in coating properties. As Comparative Example 1-1, solubility test of the silicone compound was conducted by using a fluorine-containing unsaturated hydrocarbon, cis-form (Z)-1,3,3,3-tetrafluoropropene (boiling point: 9° C.). With this, it was not possible to obtain a sufficient solubility, and therefore the application was not successful.

Example 2 (Examples 2-1 to 2-2) and Comparative Example 2-1

TABLE 2

| | Solvent comp. (mass %) | | Silicone oil added | Conc. of silicone compound | | | |
|---|---|---|---|---|---|---|---|
| | 1233Z | 254pc | (g) | (mass %) | Solubility | Drying characteristics | Coating properties |
| Ex. 2-1 | 65 | 35 | 0.1-80 | 0.5-80 | dissolved | good | good |
| Ex. 2-2 | 50 | 50 | 0.1-80 | 0.5-80 | dissolved | good | good |
| Com. Ex. 2-1 | 0 | 100 | 0.1 | 0.5 | undissolved | — | — |

1233Z: (Z)-1-chloro-3,3,3-trifluoropropene
254pc: 1,1,2,2-tetrafluoro-1-methoxyethane Example 3 (Examples 3-1 to 3-3) and Comparative Example 3-1

TABLE 3

| | Solvent comp. (mass %) | | Silicone oil added | Conc. of silicone compound | | | |
|---|---|---|---|---|---|---|---|
| | 1233E | 254pc | (g) | (mass %) | Solubility | Drying characteristics | Coating properties |
| Ex. 3-1 | 60 | 40 | 0.1-80 | 0.5-80 | dissolved | good | good |
| Ex. 3-2 | 50 | 50 | 0.1-80 | 0.5-80 | dissolved | good | good |
| Ex. 3-3 | 40 | 60 | 0.1-80 | 0.5-80 | dissolved | good | good |
| Com. Ex. 3-1 | 0 | 100 | 0.1 | 0.5 | undissolved | — | — |

1233E: (E)-1-chloro-3,3,3-trifluoropropene
254pc: 1,1,2,2-tetrafluoro-1-methoxyethane

TABLE 4

| | Solvent comp. (mass %) | | Silicone oil added | Conc. of silicone compound | | | |
|---|---|---|---|---|---|---|---|
| | 1233Z | 365mfc | (g) | (mass %) | Solubility | Drying characteristics | Coating properties |
| Ex. 4-1 | 70 | 30 | 0.1-80 | 0.5-80 | dissolved | good | good |
| Ex. 4-2 | 60 | 40 | 0.1-80 | 0.5-80 | dissolved | good | good |
| Com. Ex. 4-1 | 0 | 100 | 0.1 | 0.5 | undissolved | — | — |

1233Z: (Z)-1-chloro-3,3,3-trifluoropropene
365mfc: 1,1,1,3,3-pentafluorobutane

Example 5 (Example 5-1) and Comparative Example 5-1

TABLE 5

| | Solvent comp. (mass %) | | Silicone oil added | Conc. of silicone compound | | | |
|---|---|---|---|---|---|---|---|
| | 1233Z | 347pc-f | (g) | (mass %) | Solubility | Drying characteristics | Coating properties |
| Ex. 5-1 | 70 | 30 | 0.1-80 | 0.5-80 | dissolved | good | good |
| Com. Ex. 5-1 | 0 | 100 | 0.1 | 0.5 | undissolved | — | — |

1233Z: (Z)-1-chloro-3,3,3-trifluoropropene
347pc-f: 1,1,2,2-tetrafluoro-1-(2,2,2-trifluoroethoxy)ethane For example, in Example 2-1 of Table 2, all of the five test samples (the amounts of the silicone oil added: 0.1 g, 1 g, 5 g, 30 g, and 80 g) showed the results of Table 2. Similarly, also in each of the other examples, all of the five test samples showed the results of Tables 2-5.

From the results of Table 2 and Table 4 to Table 5, even in cases that other compositions, such as 1,1,2,2-tetrafluoro-1-methoxyethane (254 pc), 1,1,1,3,3-pentafluorobutane (365mfc), and 1,1,2,2-tetrafluoro-1-(2,2,2-trifluoroethoxy) ethane (347 pc-f), were added to cis-form (Z)-1-chloro-3,3,3-trifluoropropene, good solubilities to the silicone compound were shown, and drying characteristics and coating properties were also good, by adjusting the mixing ratio.

Furthermore, from Table 2 and Table 3, even in the case of using either cis form (Z configuration) or trans form (E configuration) as 1-chloro-3,3,3-trifluoropropene, it is good in solubility, drying characteristics and coating properties of the silicone compound. Therefore, it is understood that cis form and trans form of 1-chloro-3,3,3-trifluoropropene have shown comparable solubilities relative to the silicone compound.

(Flammability Test)

By using a tag closed flash point tester (TAG-E type, made by Yoshida Kagaku Co.), the measurement of flash point was conducted on the solvent composition for silicone compounds in the present invention.

There was conducted the flash point measurement of the solvent composition for silicone compounds of 1-chloro-3,3,3-trifluoropropene and 1,1,2,2-tetrafluoro-1-methoxyethane (HFE-254 pc). The flash point was measured in both cases of cis form (1233Z) and trans form (1233E) as 1-chloro-3,3,3-trifluoropropene.

As each composition, there was used each of the compositions of 1233Z/254 pc=40/60 (mass ratio), 30/70 (mass ratio), 20/80 (mass ratio) and 15/85 (mass ratio), 1233E/254 pc=40/60 (mass ratio), 35/65 (mass ratio) and 20/80 (mass ratio), and 254 pc alone as a reference example. The temperature rise rate in the flash point measurement was set at 1° C./min. The results are shown in Tables 6 and 7.

From the results of Tables 6 and 7, flash point was not found in proportions of 1233Z/254 pc=40/60 (mass ratio) and 30/70 (mass ratio), and 1233E/254 pc=40/60 (mass ratio) and 35/65 (mass ratio). On the other hand, in proportions of 1233Z/254 pc=20/80 (mass ratio) and 15/85 (mass ratio), and 1233E/254 pc=20/80 (mass ratio), the flash points were respectively 30° C., 21° C. and −6° C.

It is understood from the results of Table 6 and Table 7 that it becomes possible to use them as solvent compositions for silicone compounds, with no flash point and easy handling, by mixing appropriate proportions of 1-chloro-3,3,3-trifluoropropene, of which flash point does not exist, with 254 pc in which alone flash point exists. For example, it is understood that flash point disappears by adding about 30 mass % or more of 1-chloro-3,3,3-trifluoropropene. Furthermore, it is understood that there is not a large difference between cis form (1233Z) and trans form (1233E) in terms of flash point.

TABLE 6

| Solvent composition (mass %) | | Flash point (° C.) |
|---|---|---|
| 1233Z | 254pc | |
| 40 | 60 | negative |
| 30 | 70 | negative |
| 20 | 80 | 30 |

TABLE 6-continued

| Solvent composition (mass %) | | Flash point (° C.) |
|---|---|---|
| 1233Z | 254pc | |
| 15 | 85 | 21 |
| 0 | 100 | −17 |

1233Z: (Z)-1-chloro-3,3,3-trifluoropropene
254pc: 1,1,2,2-tetrafluoro-1-methoxyethane

TABLE 7

| Solvent composition (mass %) | | Flash point (° C.) |
|---|---|---|
| 1233E | 254pc | |
| 40 | 60 | negative |
| 35 | 65 | negative |
| 20 | 80 | −6 |

1233E: (E)-1-chloro-3,3,3-trifluoropropene
254pc: 1,1,2,2-tetrafluoro-1-methoxyethane Similarly, there was conducted the flash point measurement of the solvent composition for silicone compounds of 1-chloro-3,3,3-trifluoropropene and 1,1,1,3,3-pentafluorobutane (365mfc). The flash point was measured in the case of cis form (1233Z) as 1-chloro-3,3,3-trifluoropropene.

As each composition, there was used each of the compositions of 1233Z/365mfc=10/90 (mass ratio) and 5/95 (mass ratio), and 365mfc alone as a reference example. The temperature rise rate in the flash point measurement was set at 1° C./min. The results are shown in Table 8.

From the results of Table 8, flash point was not found in proportions of 1233Z/365mfc=10/90 (mass ratio) and 5/95 (mass ratio).

It is understood from the results of Table 8 that the compositions prepared by mixing 1233Z and 365mfc have almost no flash point, and therefore handling is very easy in wide mixing composition ratios. It is understood that flash point can be eliminated by adding 5 mass % or more of 1233Z.

TABLE 8

| Solvent composition (mass %) | | Flash point (° C.) |
|---|---|---|
| 1233Z | 365mfc | |
| 10 | 90 | negative |
| 5 | 95 | negative |
| 0 | 100 | 34 |

1233Z: (Z)-1-chloro-3,3,3-trifluoropropene
365mfc: 1,1,1,3,3-pentafluorobutane
365mfc: 1,1,1,3,3-pentafluorobutane

The invention claimed is:

1. A method for producing a silicone compound coating solution, comprising adding a silicone compound to a solvent composition consisting of 1-chloro-3,3,3-trifluoropropene.

2. A method for producing a silicone compound coating solution, comprising adding a silicone compound to a solvent composition comprising:
(A) 1-chloro-3,3,3-trifluoropropene and
(B) at least one compound selected from the group consisting of 1,1,1,3,3-pentafluorobutaneand 1,1,2,2-tetrafluoro-1-(2,2,2-trifluoroethoxy)ethane.

3. A method according to claim 2, wherein the solvent composition comprises 60-80 mass % of the 1-chloro-3,3,3-trifluoropropene and 40-20 mass % of the 1,1,1,3,3-pentafluorobutane.

4. A method according to claim 2, wherein the solvent composition comprises 70-80 mass % of the 1-chloro-3,3,3-trifluoropropene and 30-20 mass % of the 1,1,2,2-tetrafluoro-1-(2,2,2-trifluoroethoxy)ethane.

5. A silicone compound coating solution, comprising:
a silicone compound and
a solvent composition for silicone compounds, the solvent composition consisting of 1-chloro-3,3,3-trifluoropropene.

6. A silicone compound coating solution according to claim 5, wherein the silicone compound is a straight silicone.

7. A method for applying a silicone compound, comprising applying the silicone compound coating solution according to claim 5 on a surface of an article, and then removing the solvent composition for silicone compounds in the silicone compound coating solution by evaporation, thereby forming a film of the silicone compound on the surface of the article.

8. A method for applying a silicone compound according to claim 7, wherein the article is metal or resin.

9. A silicone compound coating solution, comprising:
a silicone compound and
a solvent composition comprising (A) 1-chloro-3,3,3-trifluoropropene and (B) at least one compound selected from the group consisting of 1,1,1,3,3-pentafluorobutane and 1,1,2,2-tetrafluoro-1-(2,2,2-trifluoro ethoxy)ethane.

10. A silicone compound coating solution according to claim 9, wherein the solvent composition comprises 60-80 mass % of the 1-chloro-3,3,3-trifluoropropene and 40-20 mass % of the 1,1,1,3,3-pentafluorobutane.

11. A silicone compound coating solution according to claim 9, wherein the solvent composition comprises 70-80 mass % of the 1-chloro-3,3,3-trifluoropropene and 30-20 mass % of the 1,1,2,2-tetrafluoro-1-(2,2,2-trifluoroethoxy)ethane.

12. A method for producing a straight-silicone coating solution, comprising: adding a straight silicone to a solvent composition comprising 1-chloro-3,3,3-trifluoropropene.

13. A method for producing a straight-silicone coating solution, comprising: adding a straight silicone to a solvent composition comprising:
(A) 1-chloro-3,3,3-trifluoropropene and
(B) at least one compound selected from the group consisting of 1,1,2,2-tetrafluoro-1-methoxyethane, 1,1,1,3,3-pentafluorobutane, and 1,1,2,2-tetrafluoro-1-(2,2,2-trifluoroethoxy)ethane.

14. A method according to claim 13, wherein the solvent composition comprises 40-80 mass % of the 1-chloro-3,3,3-trifluoropropene and 60-20 mass % of the 1,1,2,2-tetrafluoro-1-methoxyethane.

15. A method according to claim 13, wherein the solvent composition comprises 60-80 mass % of the 1-chloro-3,3,3-trifluoropropene and 40-20 mass % of the 1,1,1,3,3-pentafluorobutane.

16. A method according to claim 13, wherein the solvent composition comprises 70-80 mass % of the 1-chloro-3,3,3-trifluoropropene and 30-20 mass % of the 1,1,2,2-tetrafluoro-1-(2,2,2-trifluoroethoxy)ethane.

17. A straight-silicone coating solution, comprising:
a straight silicone and
a solvent composition comprising 1-chloro-3,3,3-trifluoropropene.

18. A straight-silicone coating solution according to claim 17, wherein the solvent composition further comprises at least one compound selected from the group consisting of 1,1,2,2-tetrafluoro-1-methoxyethane, 1,1,1,3,3-pentafluorobutane, and 1,1,2,2-tetrafluoro-1-(2,2,2-trifluoroethoxy)ethane.

19. A straight-silicone coating solution according to claim 18, wherein the solvent composition comprises 40-80 mass % of the 1-chloro-3,3,3-trifluoropropene and 60-20 mass % of the 1,1,2,2-tetrafluoro-1-methoxyethane.

20. A straight-silicone coating solution according to claim 18, wherein the composition comprises 60-80 mass % of the 1-chloro-3,3,3-trifluoropropene and 40-20 mass % of the 1,1,1,3,3-pentafluorobutane.

21. A straight-silicone coating solution according to claim 18, wherein the solvent composition comprises 70-80 mass % of the 1-chloro-3,3,3-trifluoropropene and 30-20 mass % of the 1,1,2,2-tetrafluoro-1-(2,2,2-trifluoroethoxy)ethane.

22. A method for applying a straight silicone, comprising applying the straight-silicone coating solution according to claim 15 on a surface of an article, and then removing the solvent composition in the straight-silicone coating solution by evaporation, thereby forming a film of the straight silicone on the surface of the article.

23. A method for applying a straight silicone according to claim 22, wherein the article is metal or resin.

* * * * *